(12) United States Patent
Tegg

(10) Patent No.: US 9,717,141 B1
(45) Date of Patent: Jul. 25, 2017

(54) FLEXIBLE PRINTED CIRCUIT WITH REMOVABLE TESTING PORTION

(71) Applicant: St. Jude Medical, Atrial Fibrillation Division, Inc., St. Paul, MN (US)

(72) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 132 days.

(21) Appl. No.: 14/108,724

(22) Filed: Dec. 17, 2013

Related U.S. Application Data

(60) Provisional application No. 61/748,653, filed on Jan. 3, 2013.

(51) Int. Cl.
   *H05K 1/00* (2006.01)
   *H05K 1/02* (2006.01)

(52) U.S. Cl.
   CPC ................... *H05K 1/0268* (2013.01)

(58) Field of Classification Search
   CPC ........... H05K 1/118; H05K 2201/0909; H05K 2201/09127; H05K 2201/09972; H05K 3/361; H05K 2201/175; H05K 2201/09063
   USPC .................................................. 174/262, 254
   See application file for complete search history.

(56) References Cited

U.S. PATENT DOCUMENTS

| | | | | |
|---|---|---|---|---|
| 3,780,431 A * | 12/1973 | Feeney | | 174/254 |
| 4,353,372 A * | 10/1982 | Ayer | | 600/393 |
| 4,831,278 A * | 5/1989 | Ueda | | B60R 16/0207 174/71 R |
| 5,233,754 A * | 8/1993 | Matsunaga | | B26D 7/08 29/413 |
| 5,594,214 A * | 1/1997 | Liao | | H05K 1/0293 174/117 A |
| 5,700,979 A * | 12/1997 | Lewis et al. | | 174/117 F |
| 6,118,665 A * | 9/2000 | Kishida | | H05K 3/361 174/117 F |
| 6,274,819 B1 * | 8/2001 | Li et al. | | 174/254 |
| 6,373,709 B1 * | 4/2002 | Hino et al. | | 174/535 |
| 6,543,673 B2 * | 4/2003 | Lennard | | G11B 5/40 361/55 |
| 6,657,606 B2 * | 12/2003 | Kang et al. | | 349/150 |
| 7,757,389 B2 * | 7/2010 | Nozaki | | H05K 1/0266 361/749 |
| 7,901,358 B2 * | 3/2011 | Mehi et al. | | 600/447 |

(Continued)

OTHER PUBLICATIONS

Definition of score from www.thefreedictionary.com, Jan. 4, 2016.*

(Continued)

*Primary Examiner* — Chau N Nguyen
*Assistant Examiner* — Roshn Varghese
(74) *Attorney, Agent, or Firm* — Dykema Gossett PLLC

(57) ABSTRACT

A flexible printed circuit which includes a flexible substrate, a plurality of conductive pads, and a plurality of conductive traces that conductively connect to at least two conductive pads. The plurality of conductive pads and traces are defined on the flexible substrate. The flexible substrate has a first portion and a second portion. The first portion has at least two sets of conductive pads. The second portion has at least one set of conductive pads and is configured to conductively connect to a testing device. After the flexible printed circuit is tested, the second portion of the flexible substrate is detached from the first portion of the flexible substrate.

20 Claims, 5 Drawing Sheets

(56) References Cited

U.S. PATENT DOCUMENTS

| | | | | |
|---|---|---|---|---|
| 2002/0020555 A1* | 2/2002 | Daido | ............... | H05K 3/0052 |
| | | | | 174/261 |
| 2003/0015349 A1* | 1/2003 | Watanabe | ............... | 174/261 |
| 2003/0223210 A1* | 12/2003 | Chin | ............... | H05K 3/0052 |
| | | | | 361/806 |
| 2007/0219551 A1* | 9/2007 | Honour | ............... | A61B 5/0422 |
| | | | | 606/41 |
| 2008/0029293 A1* | 2/2008 | Ooyabu et al. | ............... | 174/250 |
| 2010/0094279 A1* | 4/2010 | Kauphusman | ............... | A61B 5/0422 |
| | | | | 29/832 |
| 2012/0276758 A1* | 11/2012 | Donauer | ............... | F21V 19/003 |
| | | | | 439/59 |

OTHER PUBLICATIONS

Definition of score from www.dictionary.reference.com, Jan. 4, 2016.*

Definition of "pad" from http://www.oxforddictionaries.com/, Apr. 12, 2016.*

Definition of "cut" from http://www.merriam-webster.com/dictionary/cut, Aug. 30, 2016.*

Definition of "cut" from http://www.thefreedictionary.com/cut, Aug. 30, 2016.*

Definition of "weaken" from http://www.thefreedictionary.com/weaken, Aug. 30, 2016.*

Definition of "weaken" from http://www.merriam-webster.com/dictionary/weaken, Aug. 30, 2016.*

* cited by examiner

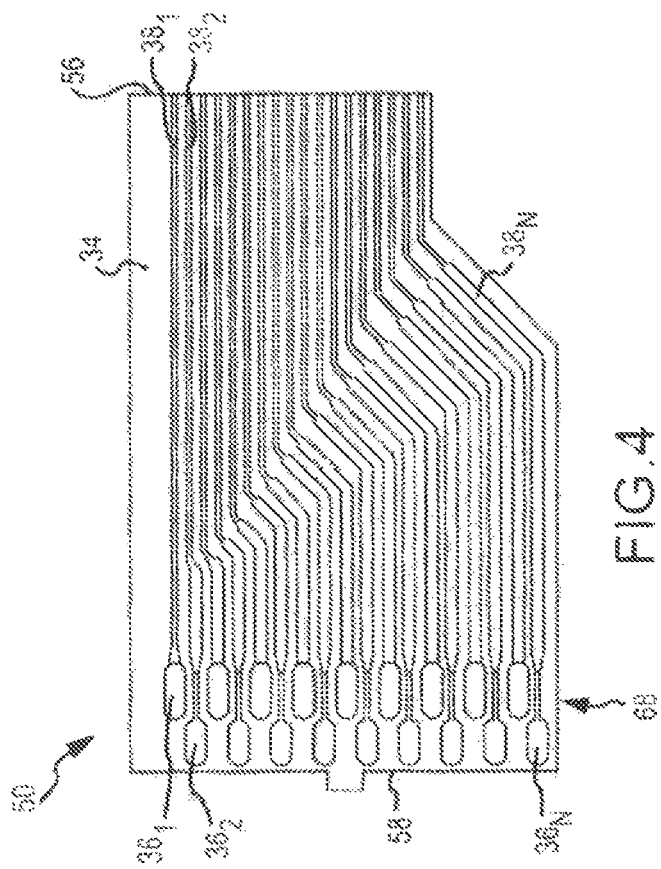
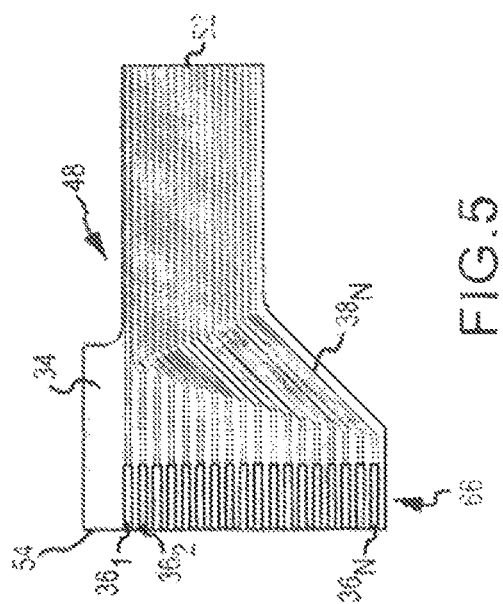

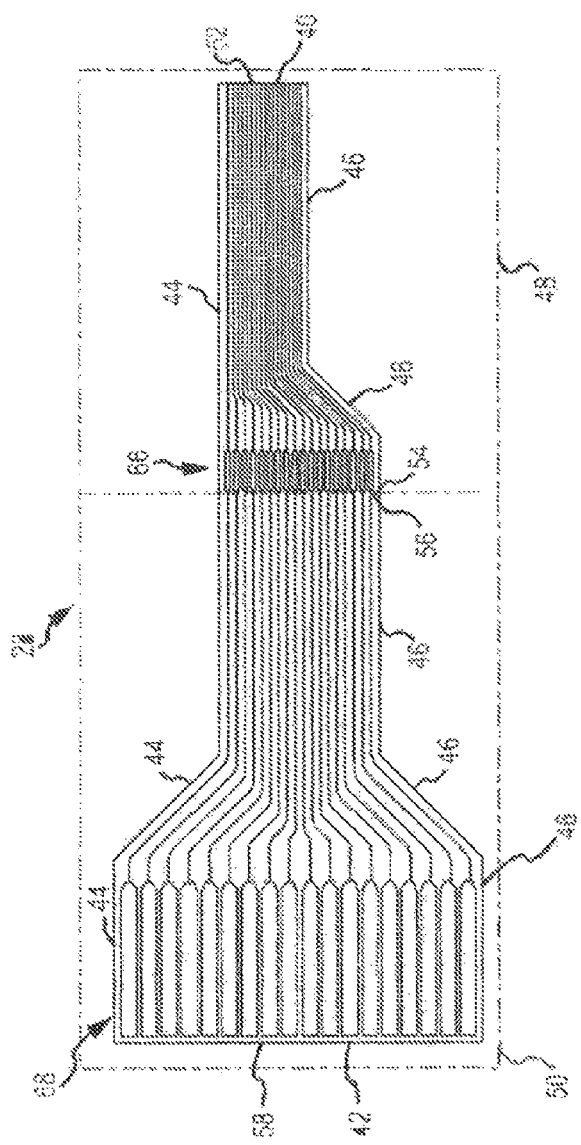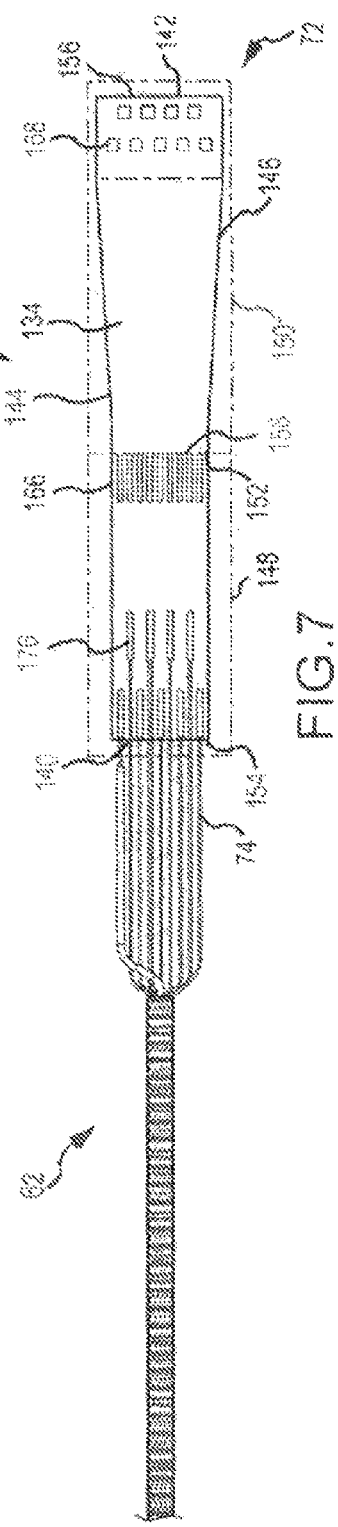

FLEXIBLE PRINTED CIRCUIT WITH REMOVABLE TESTING PORTION

CROSS-REFERENCE TO RELATED APPLICATION

This application claims the benefit of U.S. provisional application No. 61/748,653, filed Jan. 3, 2013, the entire contents of which are hereby incorporated by reference.

BACKGROUND a. Field

This disclosure relates generally to the field of medical devices, including a medical device for introduction into a body, such as a catheter, and other maneuverable medical devices.

b. Background Art

Catheters and sheaths having flexible tubular bodies with deflectable distal ends and control handles for controlling distal end deflection are commonly used in connection with many noninvasive medical procedures. For example, catheters having one or more ultrasound transducers along the distal ends of their bodies are used for intra-cardiac echocardiography studies. The distal end of the catheter body is typically positioned in a patient's heart and an ultrasound transducer may provide signal data which may be used to generate images to visualize cardiac structures and blood flow within the heart during intra-cardiac visualization, navigation, and mapping. Generally, an ultrasound transducer may comprise one piezoelectric element or a plurality of piezoelectric elements. Each piezoelectric element may have a relatively fine electrically conductive wire attached thereto, and the wire may extend through the catheter body, ultimately to an electronic control unit (ECU). For example, the conductive wire may extend from the distal end to a proximal end of the catheter where the wire may be terminated with an electrical connector that can be configured to connect with a corresponding socket provided in an ECU. To organize a plurality of wires running throughout the catheter body, the wires may be positioned and attached on a flat mylar ribbon.

As the components of the medical device increase in complexity, as well as cost, it may be desirable to operatively or conductively connect the various components to testing equipment prior to final assembly of the medical device.

The foregoing discussion is intended only to illustrate the present field and should not be taken as a disavowal of claim scope.

BRIEF SUMMARY

A flexible printed circuit for a medical device may comprise a flexible substrate, a plurality of conductive pads, and a plurality of conductive traces. The flexible substrate may have a first portion and a second portion. A plurality of conductive pads may be defined on the flexible substrate. The plurality of conductive traces may be defined on the flexible substrate and conductively connect at least one conductive pad to another conductive pad. At least one conductive pad located on the second portion of the flexible substrate may be configured to conductively connect to a testing device, and the second portion of the flexible substrate may be detached from the first portion of the flexible substrate.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 4 is an illustration of the detached removable portion of the embodiment of the flexible printed circuit of FIG. 3

FIG. 5 is an illustration of the embodiment of the flexible printed circuit of FIG. 3 after the removable portion has been detached.

FIG. 6 is an illustration of an embodiment of a flexible printed circuit with a removable portion.

FIG. 7 is an illustration of an embodiment of a flexible printed circuit of a wire harness.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting or absolute.

Figure 1:
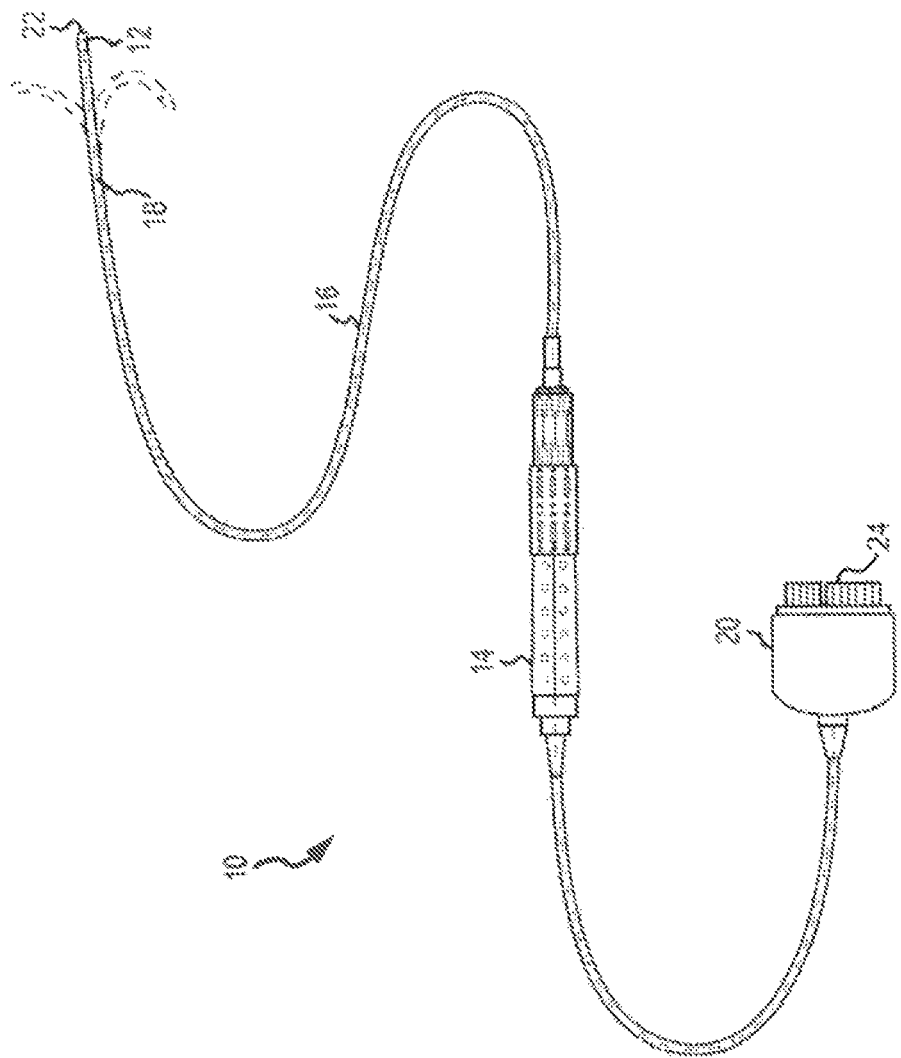
FIG. 1 generally illustrates an embodiment of a catheter having an ultrasound transducer assembly, body, handle, electrical connector, and wire harness.

Referring now to the drawings wherein like reference numerals are used to identify identical components in the various views, FIG. 1 generally illustrates an exemplary embodiment of a catheter 10 for performing one or more diagnostic and/or therapeutic functions. For example, the catheter 10 may include components for performing intracardiac echocardiography ("ICE") procedures. It should be understood, however, that while the description below is respect to an ICE catheter 10, the subject matter of the disclosure may find application in connection with a variety of medical devices. As generally illustrated in FIG. 1, a catheter 10 may comprise an ultrasound transducer assembly 12, a handle 14, a body 16, a wire harness 18, and an electrical connector 20 configured to connect to an electronic control unit (ECU), such as, for example and without limitation, the ViewMate™ Z or ViewMate™ II intracardiac ultrasound consoles via the compatible ViewFlex™ Catheter Interface Module commercialized by St. Jude Medical, Inc. In an embodiment, the ultrasound console may have a system frequency of 4.5-8.5 MHz. In another embodiment, the system frequency may be 3.0-9.0 MHz. In an embodiment, the ultrasound console may have a viewing angle of 90° F. In another embodiment, the viewing angle may be 80° F. In an embodiment, the ultrasound consoles may have a maximum viewing depth of 18 cm. The catheter 10 may have a distal end 22 and a proximal end 24, where the ultrasound transducer assembly 12 may be located proximate the distal end 22.

Figure 2:
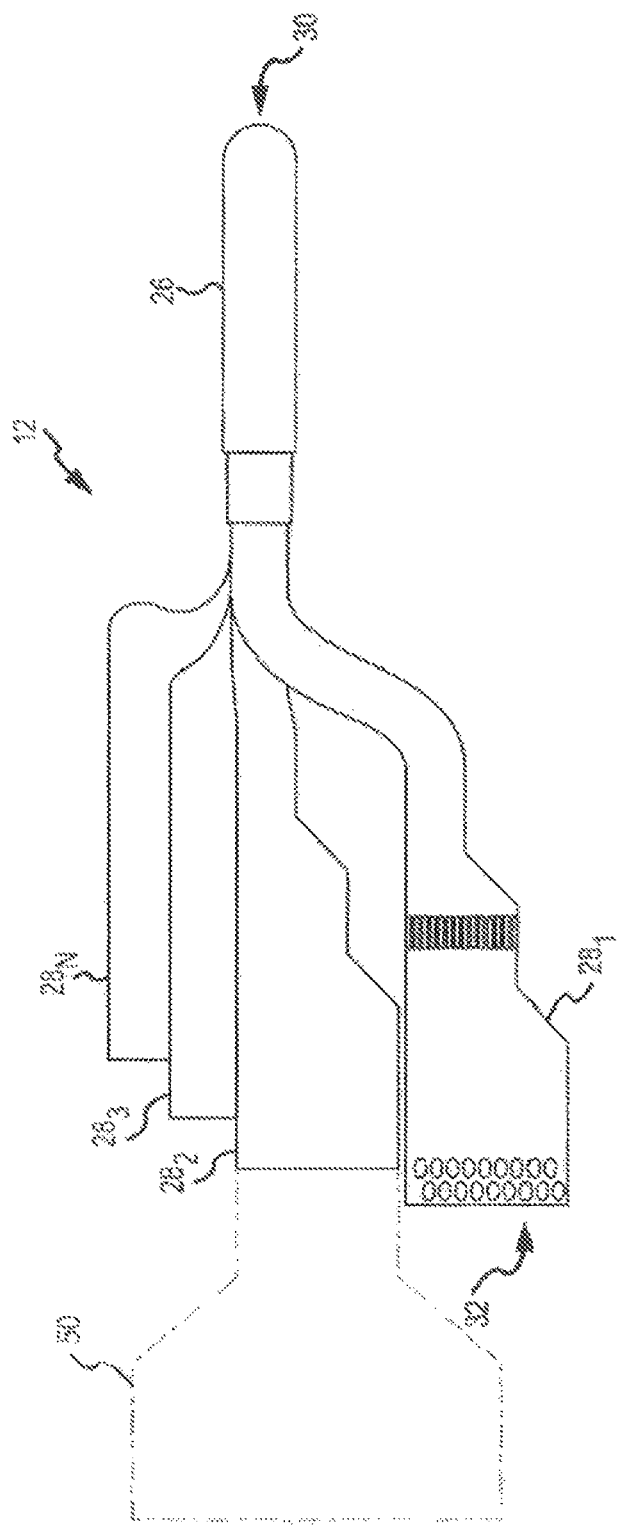
FIG. 2 is an illustration of an embodiment of the ultrasound transducer assembly of FIG. 1.

Referring to FIG. 2, an ultrasound transducer assembly 12 may comprise a ultrasound transducer 26 and a plurality of flexible printed circuits 28. As used herein, "flexible printed circuits 28" or "flexible printed circuit 28" may refer to one or more flexible printed circuits $28_1$, $28_2$, . . . $28_N$, as appropriate and as generally illustrated The ultrasound transducer 26 may include a plurality of piezoelectric elements that are operatively or conductively connected to the plurality of flexible printed circuits 28. In an embodiment, each piezoelectric element may include a conductive trace, and the conductive trace of the piezoelectric element may be bonded to a predefined conductive trace on the flexible printed circuits via trace-to-trace bonding. The ultrasound transducer assembly may have a distal end 30 and a proximal end 32.

Referring to FIGS. 3-6, each flexible printed circuit 28 may comprise a flexible substrate 34, a plurality of conductive pads 36, and a plurality of conductive traces 38 defined on the substrate 34, where the conductive traces 38 may be used to conductively connect the conductive pads 36. As used herein, "conductive pads 36" or "conductive pad 36" may refer to one or more conductive pads $36_1$, $36_2$, . . . $36_N$ as appropriate and as generally illustrated. Additionally, as used herein, "conductive traces 38" or "conductive trace 38" may refer to one or more conductive traces $38_1$, $38_2$, . . . $38_N$ as appropriate and as generally illustrated.

Figure 3:
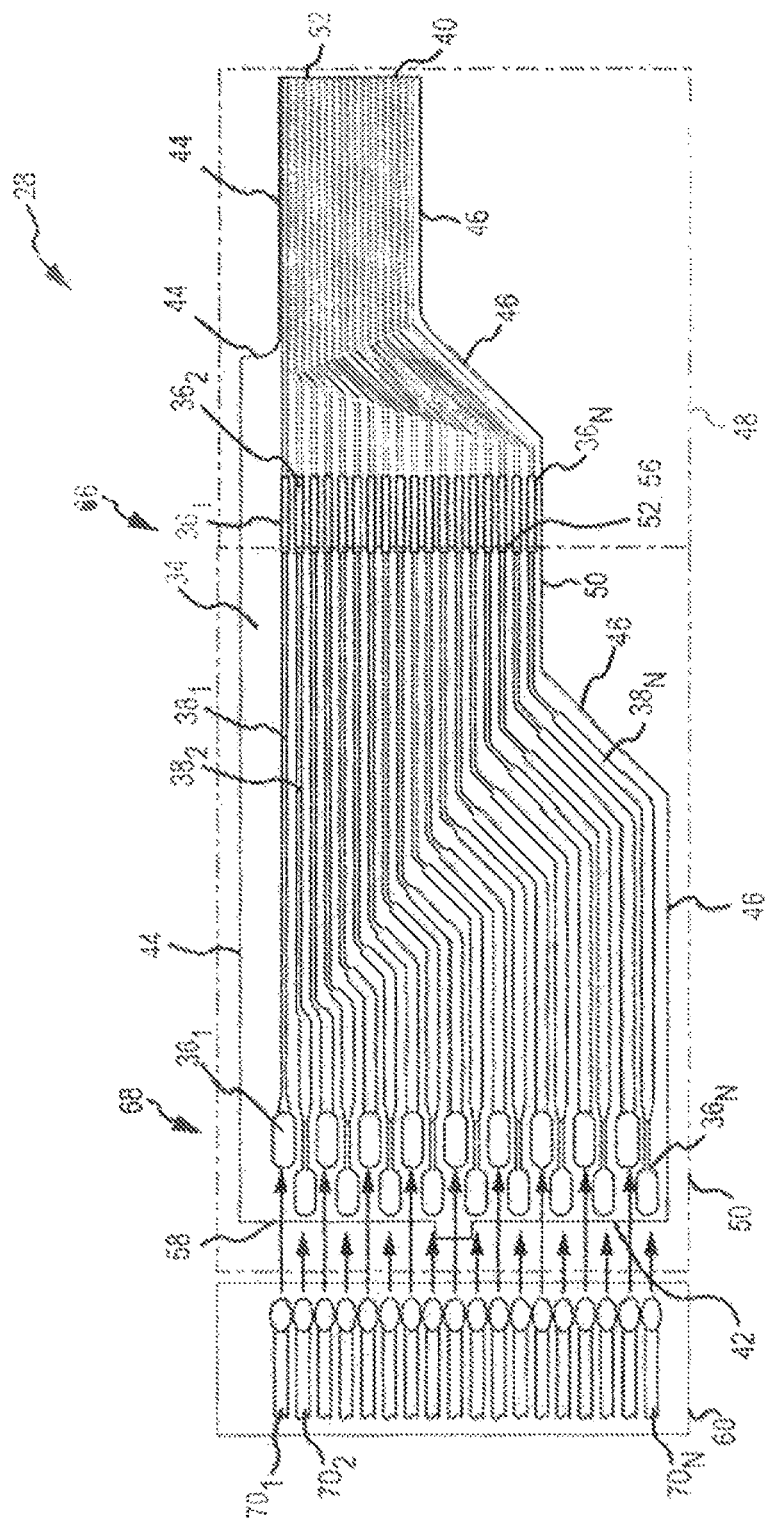
FIG. 3 is an illustration of an embodiment of a flexible printed circuit with a removable portion.

The flexible substrate 34 may have a generally thin thickness (cross-section area) which may allow the flexible substrate 34 to flex, bend, and fold. The shape of the flexible substrate 34 may be defined by a first edge 40, a second edge 42, a third edge 44, and a fourth edge 46. The first edge 40 (or distal edge) may be located closest to the transducer. The second edge 42 (or proximal edge) may be located opposite the first edge 40. The third and fourth edges 44, 46 may be each adjacent the first and second edges 40, 42, and the third and fourth edges 44, 46 may each connect to the first and second edges 40, 42. In an embodiment, the second edge 42 may be longer in length than the first edge 40. As generally illustrated in FIGS. 3 and 6, the first edge 40, second edge 42, third edge 44, or fourth edge 46 may bend as necessary to form various shapes and the edges 40, 42, 44, 46 do not have to be straight. In an embodiment, as generally illustrated in FIG. 3, the fourth edge 46 may substantially flare away from the third edge 44. In another embodiment as generally illustrated in FIG. 6, both the third and fourth edges 44, 46 may flare away from each other. Flaring various edges, such as the third or fourth edges 44, 46, may increase the width of the flexible printed circuit 28.

In an embodiment, the flexible substrate 34 may include a first portion 48 and a second portion 50, each portion 48, 50 having a width defined by the distance between the third and fourth edges 44, 46. The first portion 48 may be located closest to the ultrasound transducer 26. The first portion 48 may have a distal end 52 and a proximal end 54, where the distal end may be closest to the ultrasound transducer 26. In an embodiment, the first portion 48 may have a wider width at the proximal end 54 of the first portion 48 than the distal end 52 of the first portion 48 as generally illustrated in FIGS. 3, 5, and 6. The width of the first portion 48 may increase as the fourth edge 46 flares away from the third edge 44, or the third edge 44 flares away from the fourth edge 46, or both the third edge 44 and fourth edge 46 flare away from each other. In an embodiment, the width of the proximal end 54 of the first portion 48 may be approximately double the width of the distal end 52 of the first portion 48 as generally illustrated in FIGS. 3, 5, and 6. While various embodiments have been described with particular widths, it is appreciated that other widths may be utilized and remain within the spirit and scope of the current disclosure.

The second portion 50 may have a distal end 56 and a proximal end 58. The distal end 55 of the second portion 50 may be integrally connected to the proximal end 54 of the first portion 48, or in other words, the first portion 48 and second portion 50 may be part of one integral flexible substrate 34. The distal end of the second portion 50 may be the same width as the proximal width of the first portion 48. In an embodiment, the second portion 50 may have a width that may be wider at the proximal end 58 than the distal end 56 as generally illustrated in FIGS. 3, 4, and 6. The width of the second portion 50 may increase as the fourth edge 46 flares away from the third edge 44. In an embodiment, the width of the proximal end 58 of the second portion 50 may be approximately 1⅓ times wider than the width of the distal end 56 of the second portion 50, as generally illustrated in FIGS. 3 and 4. In another embodiment, the width of the proximal end 58 of the second portion 50 may be approximately double the width of the distal end 56 of the second portion 50, as generally illustrated in FIG. 6. While various embodiments have been described with particular widths, it is appreciated that other widths may be utilized and remain within the spirit and scope of the current disclosure.

In an embodiment, the first and second portions 48, 50 may each have a surface area, where the surface area of the second portion 50 may be larger than the surface area of the first portion 48. In an embodiment, the flexible substrate 34 may be configured such that the second portion 50 may be removed or detached. In an embodiment, the flexible substrate 34 may be configured (e.g., scored) on a surface opposite a surface defined with the conductive pads 36 and conductive traces 38 to create a weakened area for promoting separation of the second portion 50 from the first portion 48. In another embodiment, the flexible substrate 34 may have visual landmarks for purposes of identifying where to remove the second portion 50. For example, a visual landmark may include, but is not limited to, an end of the plurality of conductive pads 36. In an embodiment, a portion of the plurality of conductive pads 36 may be removed. In an exemplary embodiment, the portion of the plurality of conductive pads 36 that may be removed is approximately five thousands of an inch (0.005 inch) off an overall length of the conductive pads 36. In an embodiment, the second portion 50 may be removed by using a tool (e.g., a razor blade). In an embodiment, the flexible substrate 34 may comprise a dielectric material, such as, but not limited to, polyimide.

The flexible printed circuit 28 may include a plurality of conductive traces 38 and a plurality of conductive pads 36 defined on the flexible substrate 34. The plurality of conductive traces 38 and the plurality of conductive pads 36 may be combined, creating trace/pad combinations configured to create electrically conductive circuits on the flexible circuit. The conductive pads 36 may be generally larger in width than the conductive traces 38. In an embodiment, the conductive pads 36 may be configured for receiving a solder joint to connect a particular wire to a particular circuit created trace/pad combination. In an embodiment, the conductive pads 36 may be configured for receiving a solder joint to connect to another set of conductive pads 36 (pad-to-pad connection). In an embodiment, the conductive pads 36 may be configured to conductively connect to a zero insertion force (ZIF) connector 60 (pad-to-connector connection). In an embodiment, the solder joint may be hand soldered, using reflow soldering (hot bar solder), or ACF bonding techniques. In an embodiment, the conductive traces 38 may be configured to conductive connect to another set of conductive traces 38 (trace-to-trace connection), such as, but not limited to, the connection from the ultrasound transducer 26 to the flexible printed circuit 28.

For example, in an exemplary embodiment, each piezoelectric element of the ultrasound transducer 26 may be operatively or conductively connected to a separate conductive pad 36 defined on the flexible substrate 34 of the flexible printed circuit 28. For example, the ultrasound transducer assembly 12 may have an ultrasound transducer 26 having sixty-four (64) piezoelectric elements and four flexible printed circuits 28 operatively or conductively connected to the ultrasound transducer 26. Each of the four flexible printed circuits 28 may, for example, include eighteen (18) conductive traces 38 and eighteen (18) conductive pads 36, wherein each individual trace 38 may be operatively or conductively connected to each individual pad 36, creating a trace/pad circuit. In such an embodiment, eighteen (18) conductive traces 38 and eighteen (18) conductive pads 36 may form eighteen (18) trace/pad circuits, wherein two trace/pad circuits may be connected to ground wires, and the remaining sixteen (16) trace/pad circuits may be connected to sixteen (16) piezoelectric elements of the ultrasound transducer. In an exemplary embodiment, the two outermost trace/pad circuits may correspond to ground wiring, and the sixteen (16) inner trace/pad circuits may correspond to sixteen (16) separate piezoelectric elements. For example, and without limitation, piezoelectric elements one (1) through sixteen (16) may correspond with a first flexible printed circuit $28_k$, piezoelectric elements seventeen (17) through thirty-two (32) may correspond with a second flexible printed circuit $28_2$, piezoelectric elements thirty-three (33) through forty-eight (48) may correspond with a third flexible printed circuit $28_3$, and piezoelectric elements forty-nine (49) through sixty-four (64) may correspond with a fourth or $N^{th}$ flexible printed circuit $28_N$. While the above exemplary embodiment describes a flexible printed circuit having sixteen (16) trace/pad circuits, any number of trace/pad circuits may be used to accommodate the number of electric circuits required by the component attached to one or more flexible printed circuits $28_N$, and will be appreciated that those embodiments remain within the spirit and scope of this disclosure.

In another embodiment, the conductive pads 36 may be configured to mate to a corresponding set of conductive pads 166 located on a different flexible printed circuit 128, such as, but not limited to, the flexible printed circuit 128 located on a wire harness 62 (an exemplary embodiment of the flexible printed circuit 128 of the wire harness 62 is generally illustrated in FIG. 7). In an exemplary embodiment, the electrically conductive bond between the flexible printed circuit 128 of the wire harness 62 and the flexible printed circuit 28 of the ultrasound transducer assembly 12 may be connected using reflow soldering (hot bar soldering). In another exemplary embodiment, an anisotropic conductive film (ACF) may be used for the electrically conductive bond by placing the ACF between the flexible printed circuit 28 of the wire harness 62 and the flexible printed circuit 28 of the ultrasound transducer assembly 12.

In an embodiment, the flexible printed circuit 28 may have a plurality of sets of conductive pads 36. In an embodiment, the flexible printed circuit may have two sets, a first set 66 and a second set 68. Each set 66, 68 may have a plurality of conductive pads 36 where the number of conductive pads 36 in each set 66, 68 may be equal to the number of defined electrical circuits (trace/pad circuits) on the flexible printed circuit 28. For example, in an exemplary embodiment, the first set 66 may have eighteen (18) conductive pads 36 and the second set 68 may have eighteen (18) conductive pads 36. Each conductive pad 36 in the various sets 66, 68 may be part of a defined circuit connected by the conductive traces 38. In other words, the first conductive pad 36 in the first set 66 may be connected to the first conductive pad 36 in the second set 68, where each conductive pad 36 is connected via conductive traces 38 and ultimately to the source of the electric signals, such as the piezoelectric elements of the ultrasound transducer. Thus, the exemplary embodiment having eighteen (18) conductive pads per set would have eighteen (18) separate circuits. While the example above describes sets having eighteen (18) conductive pads, it will be appreciated that the present disclosure is not meant to be so limited. Rather, other exemplary embodiments may use any number of conductive pads 36 per set to accommodate the desired amount of electrical circuits. Accordingly, it will be appreciated that embodiments other than those described with particularity herein remain within the spirit and scope of the present disclosure.

In an embodiment, the first set 66 of conductive pads 36 may be located on the first portion 48 of the flexible substrate 34. The first set 66 of conductive pads 36 may be positioned proximate the proximal end 54 of the first portion 48. The second set 68 of conductive pads 36 may be located on the second portion 50 of the flexible substrate 34 and may be positioned proximate the proximal end 58 of the second portion 50.

Prior to connecting the flexible printed circuit 28 to the ultimate intended device, such as, but not limited to, the ultrasound transducer assembly 12 to the wire harness 62, the second set 68 of conductive pads 36 may be used for testing, such as electrical testing. The second set 68 of conductive pads 36 may be located on the second portion 50 of the flexible printed circuit 28, which may be wider than the first portion 48. The larger width of the second portion 50 allows the second set 68 of conductive pads 36 to be larger in size than the corresponding conductive pads 36 in the first set 66. The larger size may be beneficial for conductively connecting the end of the flexible printed circuit 28 to testing equipment because the pitch (e.g., the spacing distance between the conductive pads 36) of the second set 68 of conductive pads 36 may be larger than the pitch of the first set 66 of conductive pads 36. For example, in an exemplary embodiment, the proximal end 58 of the second portion 50 of the flexible printed circuit 28 may be placed into the ZIF connector 60 of the testing equipment, where each conductive pad 36 in the second set 68 of conductive pads 36 coincides with a testing circuit 70 of the testing equipment. After the flexible printed circuit 28 is placed in the ZIF connector 60, the ZIF connector 60 may be closed, causing the ZIF connector 60 to grip the second set 68 of conductive pads 36, creating a conductive connection between the testing equipment and the component having the flexible printed circuit 28, such as, but not limited to, the ultrasound transducer assembly 12. The test equipment may, among others, test for continuity and isolation of the circuits and functional operability of the component (such as, but not limited to, the ultrasound transducer assembly 12 and the wire harness 62) operatively or conductively connected to the circuits. The testing allows for individual component testing prior to the assembly of the overall device, such as, but not limited to the catheter 10. Testing the individual components prior to assembly may allow for detection of nonconforming individual components and may prevent having to scrap out a completely assembled device having a nonconforming component. For example, the ultrasound transducer assembly 12 may be connected to the ZIF connector 60 of the testing equipment via the second set 68 of conductive pads 36 to confirm that the ultrasound transducer assembly 12 operates as desired. If the ultrasound transducer assembly 12 were determined to be nonconforming, the nonconforming ultrasound transducer assembly 12 may be scrapped. In contrast, if the first testing of the ultrasound transducer assembly 12 were to occur after the device (such as, but not limited to, the catheter 10) had been completely assembled, then the entire device having the nonconforming ultrasound transducer assembly 12 would have to be scrapped, thereby increasing scrap costs. Additionally, after the set of conductive pads 36 have been connected to the ZIF connector 60, the conductive pads 36 may have slight indentations from the contact with the ZIF connector 60. Therefore, it may be beneficial to use a different set of conductive pads 36 when connecting the flexible printed circuit 28 to the finished assembly of the medical device 10.

Referring to FIGS. 4 and 5, after the testing process has been completed, the second portion 50 of the flexible printed circuit 28 (as generally illustrated in FIG. 4) may be separated from the first portion 48 of the flexible printed circuit 28 (as generally illustrated in FIG. 5) including, but not limited to, cutting, breaking off, or snapping off the second portion 50 from the first portion 48. After the second portion 50 of the flexible substrate 34 has been removed from the first portion 48 of the substrate 34, the first set 66 of conductive pads 36 located at the proximal end 54 of the first portion 48 may be used to operatively or conductively connect the flexible printed circuit 28 to the ultimate intended device using the techniques described above, such as, but not limited to, reflow (hot bar) soldering or ACF. For example, in an exemplary embodiment, the flexible printed circuit 28 of the ultrasound transducer assembly 12 may be connected to the wire harness 62 by operatively or conductively connecting the first set 66 of conductive pads 36 to a corresponding set of conductive pads 36 located on a flexible printed circuit 128 of the wire harness 62 using reflow (hot bar) soldering.

While various embodiments of flexible printed circuits 28 used with an ultrasound transducer 26 have been disclosed, the flexible printed circuit 28 with a removable test area (second portion) 50 as described herein may be used with other components of an overall device 10 and oriented accordingly. For example, the wire harness 62 operatively or conductively connected to the ultrasound transducer assembly 12 may have the flexible printed circuit 128 with a removable test area 150 which may allow testing of the wire harness 62 prior to connection to the ultrasound transducer assembly 12.

Referring to FIG. 7, an embodiment of the wire harness 62 may have the flexible printed circuit 128 on the distal end of the wire harness 62. The flexible printed circuit 128 may have a removable test portion 150. For example, the flexible printed circuit 128 of the wire harness 62 may have flexible substrate 134 defined by a first edge 140, a second edge 142, a third edge 144, and a fourth edge 146. The first edge 140 (or proximal edge in this particular embodiment) may be located closest to a plurality of wires 74 of the wire harness 62. The second edge 142 (or distal edge in this particular embodiment) may be located opposite the first edge 140. The third and fourth edges 144, 146 may be each adjacent the first and second edges 140, 142, and the third and fourth edges 144, 146 may each connect to the first and second edges 140, 142.

The flexible substrate 134 may have a first portion 148 and a second portion 150, where each portion may have a width defined by the distance between the third and fourth edges 144, 146. The first portion 148 may be located closest to the plurality of wires 74. The first portion 148 may have a distal end 152 and a proximal end 154, where the proximal end 154 may be closest to the plurality of wires 74. In an embodiment, the first portion 148 may be substantially rectangular in shape, as generally illustrated in FIG. 7. While the first portion 148 has been described as a particular shape, it is appreciated that other shapes may be utilized and remain within the spirit and scope of the present disclosure.

The second portion 150 may have a distal end 156 and a proximal end 158. The proximal end 158 of the second portion 150 may be integrally connected to the distal end 152 of the first portion 48, or in other words, the first portion 148 and second portion 150 may be part of one integral flexible substrate 134. The proximal end 158 of the second portion 150 may be the same width as the distal end 152 of the first portion 148. In an embodiment, the second portion 150 may have a width that may be wider at the distal end 156 than the proximal end 158, as generally illustrated in FIG. 7. The width of the second portion 50 may increase as the third edge 144 and/or fourth edge 146 flares away from each other. In an embodiment, both the third edge 144 and the fourth edge 146 may flare away from each other, as generally illustrated in FIG. 7.

The flexible printed circuit 128 of the wire harness 62 may have three sets 166, 168, 176 of conductive pads 36, where a corresponding conductive pad 36 from each set 166, 168, 176 may be connected by a conductive trace 38. The first portion 148 may have a first set 166 and a third set 176 of conductive pads 36, where the first set 166 may be proximately located on the distal end 152 of the first portion 148 and the third set 176 may be proximately located on a proximal end 154 of the first portion 148. The third set 176 of conductive pads 36 may be conductively connected to the wiring 74 of the wire harness 62. The conductive connection of the wiring 74 of the wire harness 62 to the third set 176 of conductive pads 36 may be covered with an epoxy for protective purposes after the conductive connection, such as soldering, has been performed. The second portion 150 may have a second set 168 of conductive pads 36 proximately located on the distal end 156 of the second portion 150. The second set 168 of conductive pads 36 may be configured for conductive connection to testing equipment. In an embodiment, the distal end 156 of the second portion 150 of the flexible circuit 128 may be configured to engage the ZIF connector 60 of the testing equipment, where the ZIF connector 60 may be configured to receive the second set 168 of conductive pads 36. After the wire harness 62 has been tested, the second portion 150 may be removed or detached from the first portion 148. The first set 166 of conductive pads 36 may then be operatively or conductively connected to another component, such as, but not limited to, the corresponding set 66 of conductive pads 36 located on the flexible circuit 28 of the ultrasound transducer assembly 12.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the embodiments as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A flexible printed circuit for an elongate medical device, the flexible printed circuit comprising:
    a flexible substrate with a first surface and a second surface including a plurality of conductive pads defined on the first surface of the flexible substrate and a plurality of conductive traces defined on the first surface of the flexible substrate, wherein the flexible substrate is folded around a portion of the elongate medical device;
    wherein the flexible substrate comprises
        a first portion,
        a second portion configured to detach from the first portion of the flexible substrate at a weakened area formed on the second surface of the flexible substrate and located between the first and the second portions, wherein the weakened area comprises a scored portion of the flexible substrate configured to promote separation of the second portion from the first portion, wherein the scored portion includes a portion of each conductive pad of the plurality of conductive pads, and
        at least two conductive pads located on the second portion of the flexible substrate are configured to conductively connect to a testing device, wherein the at least two conductive pads include a removable portion that is removed during the separation of the second portion from the first portion
    wherein the flexible substrate is defined by a first, distal edge, a second, proximal edge, a third edge, and a fourth edge, where the third and the fourth edges are adjacent to the first and the second edges and the third and the fourth edges are coupled with the first and the second edges.

2. The flexible printed circuit of claim 1, wherein a length of the second edge is greater than a length of the first edge.

3. The flexible printed circuit of claim 1, wherein at least one of the third and fourth edges are flared.

4. The flexible printed circuit of claim 1, wherein the first and second portions each comprise a width defined by a distance between the third and fourth edges, and wherein a proximal end of the second portion has a width of at least $1\frac{1}{3}$ times wider than a width of a distal end of the first portion.

5. The flexible printed circuit of claim 1, wherein the at least two conductive pads are configured to conductively connect to a zero insertion force connector.

6. The flexible printed circuit of claim 1, wherein the conductive traces are configured to conductively connect to another set of conductive traces located on another flexible printed circuit.

7. The flexible printed circuit of claim 1, wherein the first portion of the flexible substrate comprises at least one conductive pad.

8. The flexible printed circuit claim 7, wherein the at least two conductive pads of the second portion are larger than the at least one conductive pad of the first portion.

9. The flexible printed circuit of claim 7, wherein:
    the at least one conductive pad of the first portion comprises a first set of conductive pads;
    the at least one conductive pad of the second portion comprises a second set of conductive pads; and
    wherein a pitch of the first set of conductive pads is less than a pitch of the second set of conductive pads.

10. The flexible printed circuit of claim 1, wherein an electrically conductive bond between the flexible printed circuit and a wire harness comprises a solder.

11. The flexible printed circuit of claim 1, wherein an electrically conductive bond between the flexible printed circuit and a wire harness comprises an anisotropic film.

12. The flexible printed circuit of claim 1, wherein the first and second portions each comprise a width defined by a distance between the third and fourth edges, and wherein a proximal end of the first portion has a width two times wider than a width of a distal end of the first portion.

13. The flexible printed circuit of claim 1, wherein the first and second portions each comprise a width defined by a distance between the third and fourth edges, and wherein a proximal end of the second portion has a width two times wider than a width of a distal end of the second portion.

14. The flexible printed circuit of claim 1, wherein the removable portion is 0.005 inches of an overall length of the conductive pad.

15. A flexible printed circuit for an elongate medical device, the flexible printed circuit comprising:
   a flexible substrate with a first surface and a second surface comprising:
      a first conductive portion including a first plurality of conductive traces on the first surface and a first plurality of conductive pads on the first surface configured to conductively connect to a testing device; and
      a second conductive portion including a second plurality of conductive traces on the first surface and a second plurality of conductive pads on the first surface;
      wherein the second conductive portion is configured to detach from the first conductive portion at a weakened area on the second surface of the flexible substrate adjacent to the first plurality of conductive pads, the weakened area comprising a scored portion of the second surface of the flexible substrate, wherein the scored portion of the flexible substrate includes a portion of each conductive pad of the plurality of conductive pads and is configured to promote separation of the second portion from the first portion, wherein the first plurality of conductive pads include a removable portion removed during the separation of the second portion from the first portion, and wherein the flexible substrate is folded around a portion of the elongate medical device, and wherein the flexible substrate is defined by a first, distal edge, a second, proximal edge, a third edge, and a fourth edge, where the third and the fourth edges are adjacent to the first and the second edges and the third and the fourth edges are coupled with the first and the second edges.

16. The flexible printed circuit of claim 15, wherein a proximal end of the second conductive portion has a width of at least 1⅓ times wider than a width of a distal end of the first conductive portion.

17. The flexible printed circuit of claim 15, wherein the conductive pads are configured to conductively connect to a zero insertion force connector.

18. The flexible printed circuit of claim 15, wherein the first plurality of conductive traces are configured to conductively connect to another set of conductive traces located on another flexible printed circuit.

19. The flexible printed circuit of claim 15, wherein each of the second plurality of conductive pads are larger than that of the first plurality of conductive pads.

20. The flexible printed circuit of claim 15, wherein a pitch of the first plurality of conductive pads is less than a pitch of the second plurality of conductive pads.

\* \* \* \* \*